United States Patent
Caffey

(10) Patent No.: US 6,296,662 B1
(45) Date of Patent: Oct. 2, 2001

(54) BIOPROSTHETIC HEART VALVE WITH BALANCED STENT POST DEFLECTION

(75) Inventor: James C. Caffey, Marble Falls, TX (US)

(73) Assignee: Sulzer Carbiomedics Inc., Austin, TX (US)

( * ) Notice: Subject to any disclaimer, the term of this patent is extended or adjusted under 35 U.S.C. 154(b) by 0 days.

(21) Appl. No.: 09/320,063

(22) Filed: May 26, 1999

(51) Int. Cl.[7] .................................................. A61F 2/24
(52) U.S. Cl. ...................... 623/2.18; 623/900; 623/2.14
(58) Field of Search ............................... 623/1.24, 1.26, 623/2.1–2.19, 900, 233, 238

(56) References Cited

U.S. PATENT DOCUMENTS

| | | | |
|---|---|---|---|
| 4,106,129 | 8/1978 | Carpentier et al. | 3/1.5 |
| 4,343,048 | 8/1982 | Ross et al. | 3/1.5 |
| 4,501,030 | 2/1985 | Lane | 3/1.5 |
| 5,037,434 | 8/1991 | Lane | 623/2 |
| 5,147,391 | * 9/1992 | Lane | 623/2.18 |
| 5,258,021 | * 11/1993 | Duran | 623/900 |
| 5,545,215 | 8/1996 | Duran | 623/2 |
| 5,562,729 | 10/1996 | Purdy et al. | 623/2 |

* cited by examiner

Primary Examiner—Bruce Snow
(74) Attorney, Agent, or Firm—Blossom E. Loo

(57) ABSTRACT

A heart valve prosthesis including a heart valve formed of a flexible material. An elongated stent member is provided in the valve and includes terminal ends. A plurality of flexible post members are formed in the stent member. Each post member includes a pair of opposite sides. A crimp collar interconnects the terminal ends of the stent member. The crimp collar is positioned between adjacent post members. A first radius is formed in the stent member between the crimp collar and an adjacent side of each adjacent post member. A plurality of second radii are formed in the stent member between an opposite side of a first one of the adjacent post members and an opposite side of a second one of the adjacent post members. The second radii are greater than each first radius.

15 Claims, 3 Drawing Sheets

BIOPROSTHETIC HEART VALVE WITH BALANCED STENT POST DEFLECTION

BACKGROUND

The disclosures herein relate generally to flexible leaflet prosthetic heart valves and more particularly to wire stents used to reinforce the valves.

Wire stents used in prosthetic heart valves are normally symmetrical in geometry, with all belly radii being equal. When a stent flat pattern is formed and joined, a crimp collar is used to join the wire ends. This results in a stiffened section between two of the adjacent posts. The stiffened section causes an imbalance in the stress levels between the various posts when equal forces are applied at the post tips, or along the posts, due to loads being experienced by the leaflet members. For example, a post opposite the crimp collar will deflect more than the posts which are adjacent the crimp collar. As a result, the difference in post deflections may affect performance and durability of the prosthetic valve leaflets.

Various stented valve devices have been proposed. U.S. Pat. No. 4,106,129 discloses a supported bioprosthetic heart valve in which the supporting stent is capable of annular deformation and also of limited perimetric expansion and contraction during heart operation. The stent includes a wire frame composed of a single flexible wire preformed to define inverted U-shaped commissure supports merging smoothly with arcuate portions connecting such supports. This device does not address the relationship between belly radii symmetry and balanced stent post deflections.

In U.S. Pat. No. 4,343,048, a stent for a cardiac valve comprises a base ring having metal legs projecting therefrom in a generally axial direction, each leg being flexible in such a manner that, when the stent has a valve installed therein and the valve is under pressure such as when operating in the heart, each respective leg can resiliently deform over substantially its whole axial length to take up strain in the valve without impairing its performance.

U.S. Pat. No. 4,501,030 discloses a prosthetic heart valve including a frame having a plurality of commissure supports, a plurality of resilient supports, and a plurality of valve leaflets. The valve leaflets are attached to the resilient supports, and the resilient supports lie radially outwardly of the commissure supports, respectively. When in use, the valve is subjected to forces which are used to clamp the valve leaflets between the resilient supports and the commissure supports to augment whatever other leaflet attachment techniques may be used. This device moves the crimp collar from the belly region to a location in the stent post area, but does not address the stent post deflection balance as a function of the belly radii. Unfortunately, known devices using wire stents have not addressed the above-mentioned imbalance condition created by the use of crimp collars.

U.S. Pat. No. 5,037,434 discloses a bioprosthetic heart valve comprising first and second mechanisms for supporting leaflets to provide multiple effective spring constants. An inner frame supporting commissures of the valve is elastic, permitting the commissures to bend in toward the center of the prosthetic heart valve at very low loads. A relatively rigid annular support ring supports the elastic frame and provides the second spring constant mechanism. An attachment system for sewing bioprosthetic leaflets to the frame and clamping the leaflets between the frame and the annular ring minimizes stress risers in the leaflets. The leaflets have an uncoupled mating edge where the leaflets meet in the center of the valve. The uncoupled portions of the leaflets permit the leaflets to roll by each other.

U.S. Pat. No. 5,545,215 discloses a frame to be placed as an external support of a biological valved conduit containing three leaflets. This external frame, made of biocompatible metal or plastic is sutured to the outer surface of the valved conduit made of biological or biocompatible membrane or sigmoid valve root in order to maintain its natural geometry. The frame has a general cylindrical configuration, circular as viewed from above and below. From a side view however, both upper and lower ends of the cylinder present three convex curvatures joined at equidistant points of the circumference. These upper and lower curves are joined by three vertical struts, so that three large saddle shaped paraboloid gaps result. The frame is a wire-like structure.

U.S. Pat. No. 5,562,729 discloses a multi-leaflet heart valve composed of biocompatible polymer which simultaneously imitates the structure and dynamics of biological heart valves. The valve includes a plurality of flexible leaflets dip cast on a mandrel. The leaflets are then bonded with a bonding agent to the interior surfaces of a plurality of struts on a metal-reinforced prosthetic stent. The leaflets open and close in response to the pumping action of the heart.

Some manufacturers of wire stented valves have ignored the imbalance problem. Others have taken approaches which do not address stent post deflection balance as a function of belly radii. Therefore, what is needed is a wire stented valve which compensates for the imbalance caused by crimp collars.

SUMMARY

One embodiment, accordingly, provides for balancing stent post deflection as a function of belly radii. To this end, a stent includes an elongated stent member having terminal ends. A plurality of flexible post members are formed in the stent member. Each post member includes a pair of opposite sides. An interconnection of the terminal ends of the stent member is provided between adjacent post members. A first radius is formed in the stent member between the interconnection and an adjacent side of each adjacent post member. A plurality of second radii are formed in the stent member between an opposite side of a first one of the adjacent post members and an opposite side of a second one of the adjacent post members. The second radii are greater than each first radius.

A principal advantage of this embodiment is that although the interconnection, e.g. a crimp collar, between the terminal ends of the stent member stiffens the stent member between adjacent posts, the resulting imbalance of flexibility of all of the posts is compensated for by an adjustment in belly radii.

BRIEF DESCRIPTION OF THE DRAWING FIGURES

DETAILED DESCRIPTION

Figure 1:
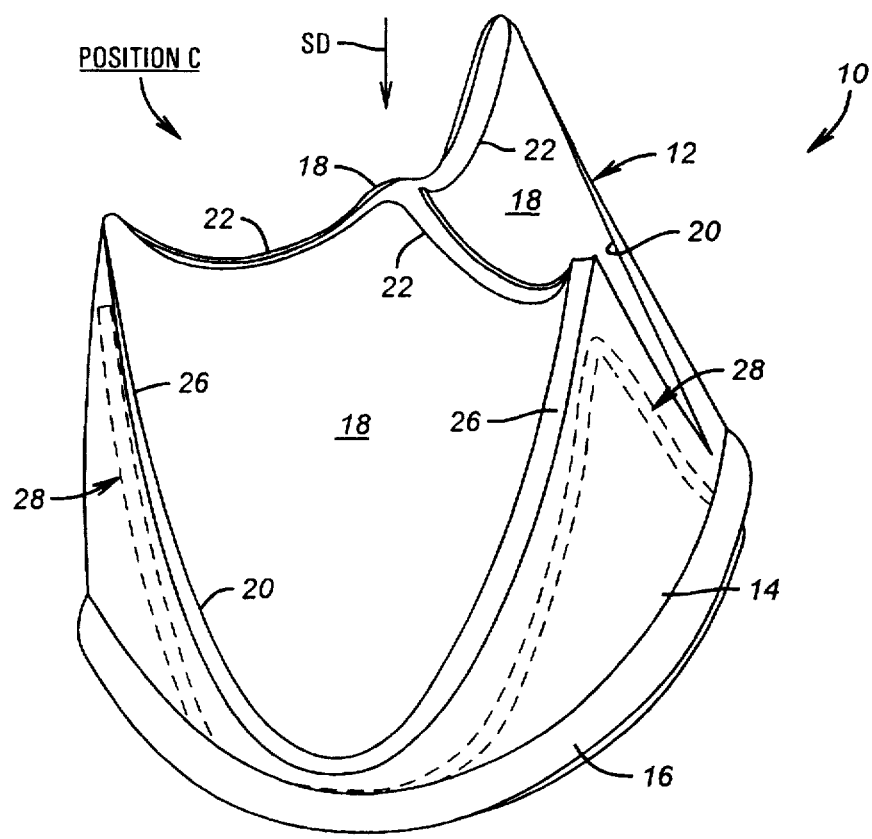
FIG. 1 is an isometric view illustrating an embodiment of a prosthetic heart valve in an at rest position.
Figure 2:
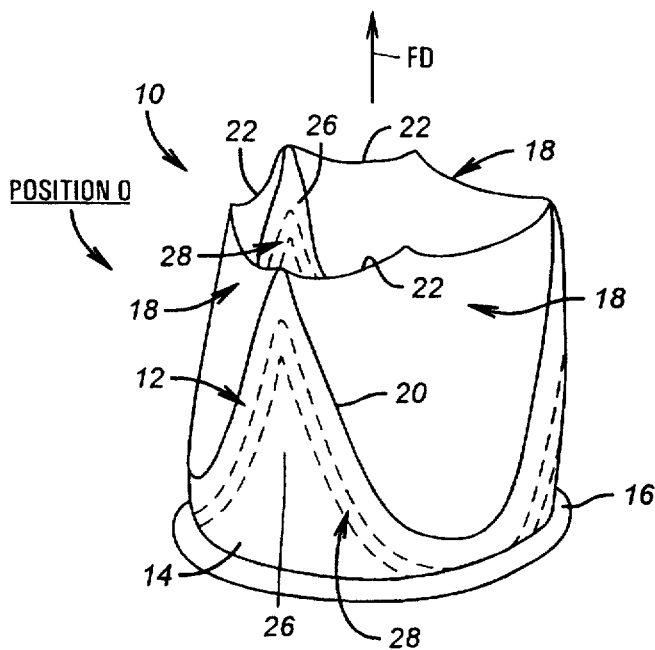
FIG. 2 is an isometric view illustrating an embodiment of a prosthetic heart valve in an open position.

A heart valve is generally designated 10 in FIG. 1. Heart valve 10 is formed as a one-piece molded biocompatible polymer body such as silicone or polyurethane and includes a generally annular peripheral body portion 12 which has a base 14. A sewing ring 16 may be formed with the base 14. Three flexible leaflets 18 are formed with body 12 and extend from an attachment curve 20 to terminate at a free margin 22. In FIG. 1, the valve is in a natural-state condition, i.e. the valve parts arc at rest and are not under the influence of any pressure acting thereon. This is in contrast with the valve after installation when the pumping action of the heart sequentially and repeatedly opens and closes the valve by urging the leaflets 18 in a first or opening direction indicated by the arrow designated FD, FIG. 2, and then in a second or closing direction, opposite the first direction, indicated by the arrow designated SD, FIG. 1.

The attachment curve 20 defines a coupling between each leaflet 18 and the peripheral body 12, and also defines a plurality of shaped posts 26 which comprise a portion of body 12 which is of a greater thickness relative to leaflets 18. A flexible stent 28, made of wire or plastic, is embedded in valve 10 by being molded into posts 26. In some configurations of molded or tissue valves, stent 28 may be secured to an outside surface of the valve body by sutures, however, the purpose of the stent in either configuration is to provide flexible reinforcement to the opening and closing valve body as described above.

Figure 3:
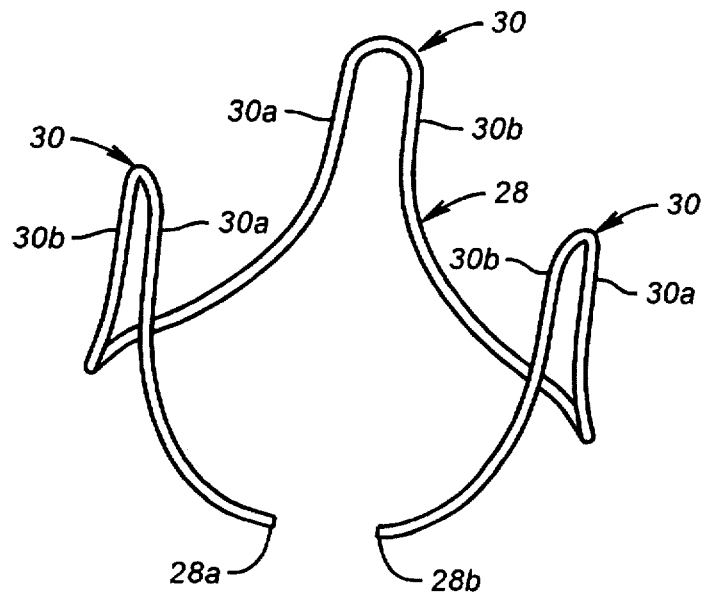
FIG. 3 is an isometric view illustrating an embodiment of a stent member having multiple posts.

Stent 28, FIG. 3, comprises an elongated stent member having terminal ends 28a and 28b, and a plurality of flexible post members 30. The post members 30 are formed into the stent 28 and each post member includes a pair of opposite sides 30a and 30b.

Figure 4:
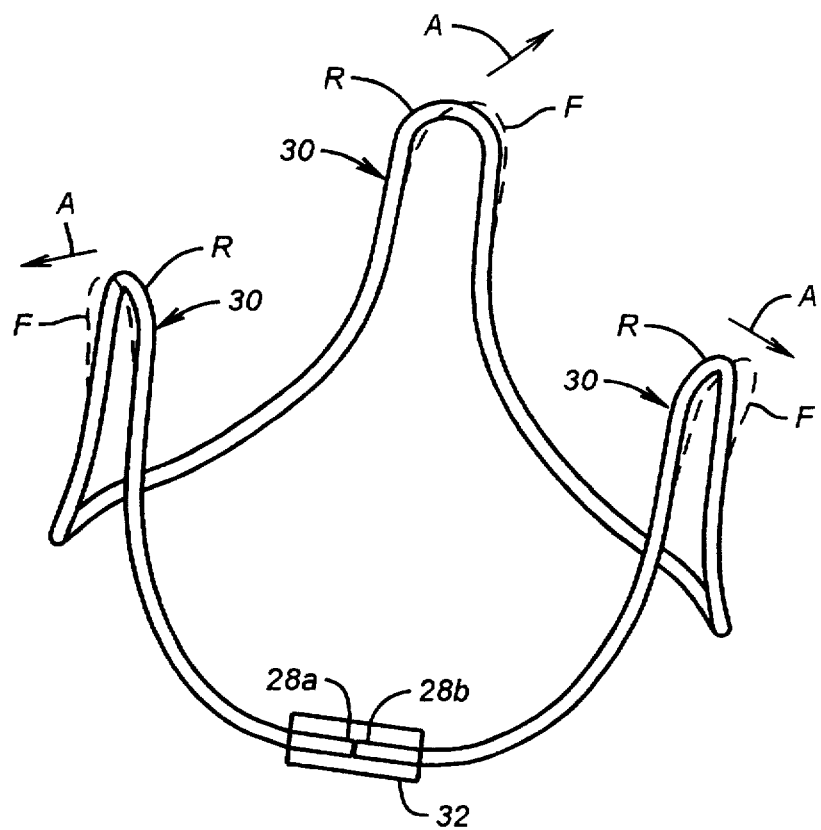
FIG. 4 is an isometric view illustrating an embodiment of a stent member including a crimp collar.

The terminal ends 28a and 28b of stent member 28 are interconnected between adjacent post members 30 by a crimp collar 32, FIG. 4. When valve 10 is in an at rest position C, FIG. 1, stent posts 30 are in a natural or at rest position R, as illustrated in solid lines in FIG. 4. When valve 10 is in an open position O, FIG. 2, stent posts 30 are flexed outwardly in the direction illustrated by a plurality of directional arrows designated A, to a flexed or broken line position F.

Figure 5:
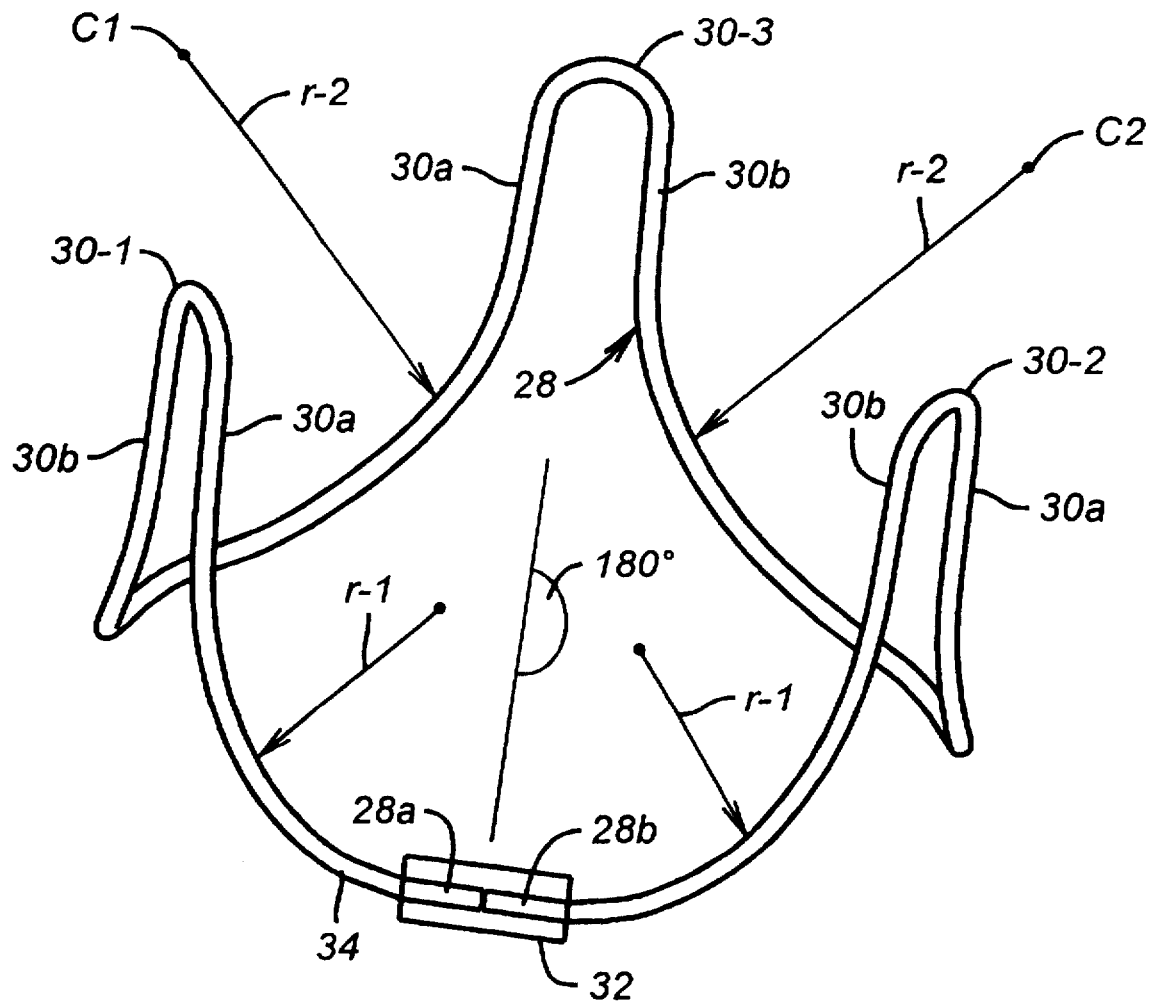
FIG. 5 is another isometric view illustrating an embodiment of a stent member.

A first belly radius r1 extending from a center C1, FIG. 5, is formed in stent 28 between the interconnection of the terminal ends 28a, 28b, i.e. at crimp collar 32, and an adjacent side of each adjacent post member 30. More specifically, side 30a of post member 30-1 is adjacent crimp collar 32, and side 30b of post member 30-2 is adjacent crimp collar 32. Post member 30-3 is between post member 30-1 and post member 30-2, and is 180° opposite crimp collar 32. Because crimp collar 32 has the effect of stiffening a section 34 of stent 28 between post members 30-1 and 30-2, this results in a stiffening of, or reducing the flexibility of adjacent post members 30-1 and 30-2. Ordinarily, all belly radii of stent member 28 are equal and therefore, post member 30-3 would, as a result, be more flexible than post members 30-1 and 30-2. This would render an imbalance in the deflection of valve 10. In order to avoid such deflection imbalance, a second belly radius r-2, adjacent sides 30a and 30b of post member 30-3 extends from a center C2 and is greater than radius r-1. Each second radius r-2 is greater than each first radius r-1 in order to decrease the flexibility of post member 30-3 with a correction which provides very close deflection values for each of the post members 30- 1, 30-2 and 30-3. Thus, the flexibility of post members 30-1, 30-2 and 30-3 is substantially the same.

In operation, belly radii r-2 are provided adjacent post member 30-3. A belly radius r-1 is provided between crimp collar 32 and post member 30-1, and another belly radius r-1 is also provided between crimp collar 32 and post member 30-2. Belly radii r-2 are greater than belly radii r-1. Therefore, very close deflection values for each post member 30-1, 30-2 and 30-3 can be achieved when equal load forces are applied to each post member 30-1 and 30-2 and 30-3.

As a result, one embodiment provides a stent including an elongated stent member having terminal ends. A plurality of flexible post members are formed in the stent member. Each post member includes a pair of opposite sides. An interconnection of the terminal ends of the stent member is positioned between adjacent post members. A first radius is formed in the stent member between the interconnection and an adjacent side of each adjacent post member. A plurality of second radii are formed in the stent member between an opposite side of a first one of the adjacent post members and an opposite side of a second one of the adjacent post members. The second radii are greater than each first radius.

Another embodiment provides a heart valve prosthesis including a heart valve formed of a flexible material. An elongated stent member is attached to the valve and includes terminal ends. A plurality of flexible post members are formed in the stent member. Each post member includes a pair of opposite sides. A crimp collar interconnects the terminal ends of the stent member. The crimp collar is positioned between adjacent post members. A first radius is formed in the stent member between the crimp collar and an adjacent side of each adjacent post member. A plurality of second radii are formed in the stent member between an opposite side of a first one of the adjacent post members and an opposite side of the second one of the adjacent post members. The second radii are greater than each first radius.

A further embodiment provides a method of shaping a stent member including forming an elongated stent member having terminal ends and including a plurality of flexible post members each having a pair of opposite sides. The terminal ends are interconnected between the adjacent post members. A first radius is formed in the stent member between the interconnected terminal ends and an adjacent side of each adjacent post member. A plurality of second radii are formed in the stent member between an opposite side of a first one of the adjacent post members and an opposite side of a second one of the adjacent post members. The second radii are greater than each first radius.

As it can be seen, the principal advantages of these embodiments are that the imbalance of flexibility of all the posts which results from the use of crimp collars, can be compensated for by an adjustment in belly radii. Thus, with the crimp collar positioned in the belly region between adjacent posts, the flat pattern pre-form, the wire forming operation, and the final crimping operation, will be more readily accomplished during manufacturing and assembly.

Although illustrative embodiments have been shown and described, a wide range of modification change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A stent comprising:
   an elongated stent member having terminal ends;
   at least three flexible post members formed in the stent member, each post member having a pair of opposite sides;

an interconnection of the terminal ends of the stent member positioned between adjacent first and second post members;

a first radius formed in the stent member between the interconnection and a side of each first or second post member adjacent the interconnection; and a plurality of second radii formed in the stent member at a side of a third post member, the second radii being greater than each first radius in an at rest position.

2. The stent as defined in claim 1 wherein a third post member is between the first post member and the second post member.

3. The stent as defined in claim 2 wherein the third post member is substantially 180° opposite the interconnection.

4. The stent as defined in claim 1 wherein each post member has substantially the same deflection under load as each other post member.

5. The stent as defined in claim 1 wherein the crimp collar and each first radius imposes a first flexibility on the first post member and the second post member and each second radius imposes a second flexibility on the third post member, the second flexibility being different from the first flexibility.

6. A heart valve prosthesis comprising:

a heart valve formed of flexible material;

an elongated stent member attached to the valve and having terminal ends;

at least three flexible post members formed in the stent member, each post member having a pair of opposite sides;

a crimp collar interconnecting the terminal ends of the stent member, the crimp collar being between adjacent first and second post members;

a first radius formed in the stent member between the crimp collar and a side of each first or second post member adjacent the crimp collar; and a plurality of second radii formed in the stent member at a side of a third post member, the second radii being greater than each first radius in an at rest position.

7. The prosthesis as defined in claim 6 wherein a third post member is between the first post member and the second post member.

8. The prosthesis as defined in claim 7 wherein the third post member is substantially 180° opposite the crimp collar.

9. The prosthesis as defined in claim 6 wherein each post member has substantially the same deflection under load as each other post member.

10. The prosthesis as defined in claim 6 wherein the crimp collar and each first radius imposes a first flexibility on the first post member and the second post member and each second radius imposes a second flexibility on the third post member, the second flexibility being different from the first flexibility, said posts having substantially the same deflection under load.

11. The prosthesis as defined in claim 7 wherein a second radius is formed in the stent member between the first post member and the third post member, and another second radius is formed in the stent member between the second post member and the third post member.

12. The prosthesis as defined in claim 7 wherein a second radius is formed in the stent member adjacent a first side of the third post member and another second radius is formed in the stent member adjacent a second side of the third post member.

13. A method of shaping a stent member comprising the steps of:

forming an elongated stent member having terminal ends and including at least three flexible post members each having a pair of opposite sides;

interconnecting the terminal ends between adjacent first and second post members;

forming a first radius formed in the stent member between interconnected terminal ends and a side of each first or second post member adjacent the terminal ends, and forming a plurality of second radii formed in the stent member at a side of a third post member, the second radii being greater than each first radius in an at rest position.

14. The method as defined in claim 12 wherein the step of interconnecting includes the step of crimping the interconnected terminal ends between the first post member and the second post member.

15. The method as defined in claim 14 wherein the step of interconnecting includes the step of positioning the interconnected terminal ends substantially 180° opposite the third post member.

* * * * *

UNITED STATES PATENT AND TRADEMARK OFFICE
CERTIFICATE OF CORRECTION

PATENT NO.   : 6,296,662 B1
DATED        : October 2, 2001
INVENTOR(S)  : Caffey It is certified that error appears in the above-identified patent and that said Letters Patent is hereby corrected as shown below:

<u>Title page,</u>
Item [73], Assignee, should read:
-- Assignee: Sulzer Carbomedics Inc., Austin, TX (US) --

Signed and Sealed this

Thirteenth Day of August, 2002

Attest:

Attesting Officer

JAMES E. ROGAN
*Director of the United States Patent and Trademark Office*